United States Patent [19]

Mendelson

[11] 4,191,183

[45] Mar. 4, 1980

[54] MIXING CHAMBER FOR USE IN PLURAL MEDICAL LIQUID INTRAVENOUS ADMINISTRATION SET

[76] Inventor: Barry Mendelson, 1 Topaz Ct., New City, N.Y. 10977

[21] Appl. No.: 847,263

[22] Filed: Oct. 31, 1977

[51] Int. Cl.$^2$ .................................................. A61M 5/00
[52] U.S. Cl. ............................... 128/214 R; 128/214 C; 141/107; 141/286; 222/145
[58] Field of Search ............ 128/214 R, 214 A, 214 C, 128/214 D, 214.2, 227, 272, 276, 215; 141/107, 286; 222/145; 366/165; 137/602

[56] References Cited

U.S. PATENT DOCUMENTS

| | | | |
|---|---|---|---|
| 967,125 | 8/1910 | Huppert | 128/229 X |
| 2,254,994 | 9/1941 | Butland | 128/214 A |
| 2,787,267 | 4/1957 | Paiano | 128/172 |
| 2,954,028 | 9/1960 | Smith | 128/214 R |
| 3,030,954 | 4/1962 | Thornton | 128/214 C |
| 3,171,412 | 3/1965 | Braun | 128/214 D |
| 3,595,231 | 7/1971 | Pistor | 128/215 |
| 3,886,937 | 6/1975 | Bobo et al. | 128/214 R |
| 3,941,126 | 3/1976 | Dietrich et al. | 128/214 R |
| 3,955,573 | 5/1976 | Hansen et al. | 128/276 |

Primary Examiner—Dalton L. Truluck
Attorney, Agent, or Firm—Martin G. Raskin

[57] ABSTRACT

A mixing chamber for use in an intravenous administration set wherein plural medical liquids are delivered to a patient comprising a pair of opposed, parallely extending front and rear walls which are closely spaced to each other relative to their transverse dimension, a top wall extending between and interconnecting the top peripheral edges of the front and rear walls and a side wall extending between and interconnecting the side peripheral edges of the front and rear walls, the front, rear, top and side walls defining a relatively shallow interior chamber. A plurality of entrance ports are formed in the top wall and an exit port is formed in the side wall. A transparent, magnifying window is provided in the front wall to provide a magnified view of the interior of the chamber. Inwardly extending shoulders are formed on the side walls to promote mixing of the plurality of medical liquids being administered to the patient. By virtue of the liquids being mixed and the improved visual access to the interior of the chamber, any precipitation resulting from mixing incompatible medical liquids is easily observed so that corrective measures may be taken.

7 Claims, 5 Drawing Figures

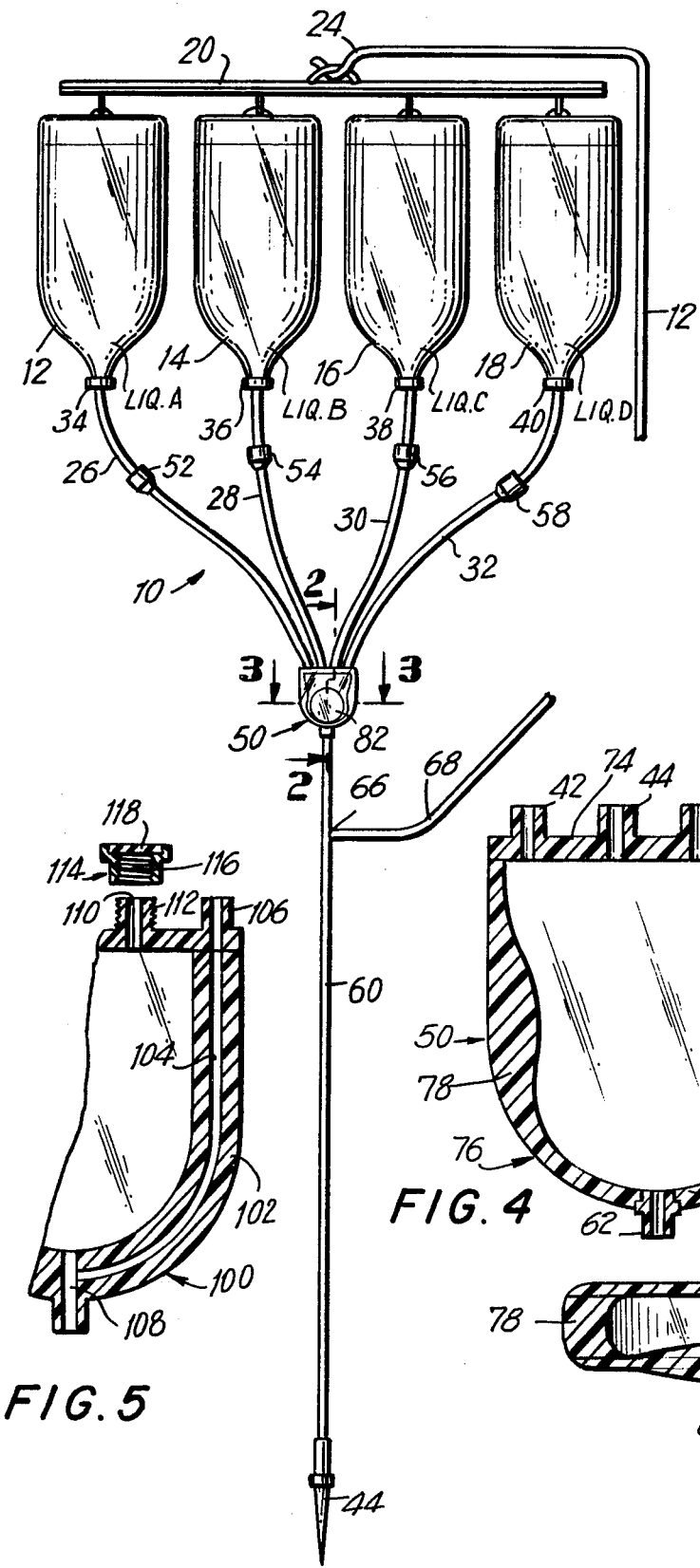
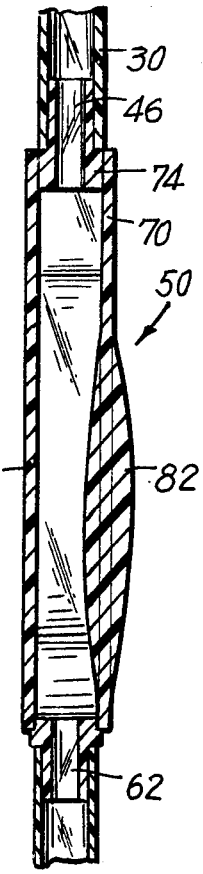
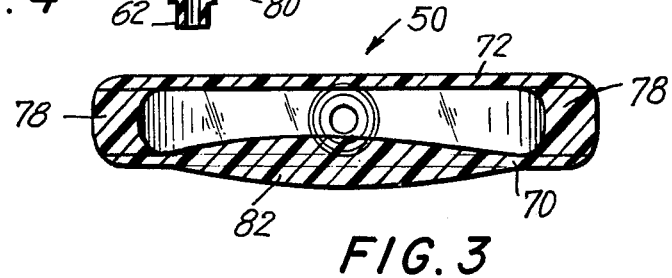

MIXING CHAMBER FOR USE IN PLURAL MEDICAL LIQUID INTRAVENOUS ADMINISTRATION SET

BACKGROUND OF THE INVENTION

This invention relates generally to intravenous administration systems and, more particularly, to systems for the administration of plural liquid medications which may have physio-chemical imcompatibilities.

The intravenous administration of medical liquids to patients is well known. Such liquids are frequently administered from a bottle which is supported in an inverted position over the patient, through a flexible delivery tube connected to the inverted bottle opening, a suitable valve mechanism, such as a manually adjustable clamp, being provided in the flexible tube system, the medical liquid flowing into the patient's vein through a venous needle. This apparatus is generally referred to as an "administration set". Medical liquids administered through such sets include normal saline, electrolytes, sugar, various pharmaceuticals, various nutritional materials, and the like.

Although great advances have been made in the development of medications and fluids to be administered intravenously to patients, a serious problem exists in such administration in that it frequently happens that two or more of such medical liquids which are to be desirably administered to a particular patient at the same time are incompatible with each other. More particularly, although such liquids may be incompatible in various respects, e.g., neutralization, antioxidants, supersaturation, etc., a serious incompatibility, and one with which the present invention is concerned, is the precipitation of small solids resulting from the mixing of two or more medical liquid. Those precipitates, if infused into the patient's vein, may have serious deleterious effects.

Precipitation resulting from mixing two incompatible medical liquids is usually difficult to detect since the reaction is kinetically slow in developing and, even after such development, it is difficult to observe since the resulting precipitate comprises particles extremely small in size. Accordingly, plural medical liquids are usually administered either using separate needles, tubing and venipuncture for each liquid or is accomplished sequentially. While the latter consumes an inordinate amount of time, the former is extremely awkward, especially when three or four such liquids are to be administered.

Thus, it would be desirable to administer the plural medical liquids simultaneously in a manner such that should any precipitation occur during the mixing of the liquids, such would be readily and immediately apparent so that corrective measures could be taken before the patient is endangered.

SUMMARY OF THE INVENTION

Accordingly, one object of the present invention is to provide a new and improved mixing chamber for use in an intravenous administration set wherein plural medical liquids are delivered to a patient.

Another object of the present invention is to provide a new and improved mixing chamber for administration of plural medical liquids wherein the mixing of such liquids is promoted so that precipitation will readily occur should such liquids be incompatible.

Still another object of the present invention is to provide a new and improved mixing chamber for use with plural medical liquids wherein any precipitation which may occur upon mixing is readily visually apparent.

Briefly, these and other objects are obtained by providing a mixing chamber including exterior walls defining a very shallow chamber relative to its transverse dimensions. A plurality of entrance ports are provided at the upper end of the mixing chamber and an exit port is provided at its lower end. The front wall of the chamber is preferably provided with a magnifying window so that the interior of the chamber may be viewed on a magnified scale so that even the slightest precipitation, which will appear as a cloudiness forming in the mixture, will be readily visually apparent. The side walls of the chamber preferably have shoulders extending therefrom inwardly into the mixing chamber to promote mixing of the medical liquids so that any precipitation which may occur will be hastened. A bypass port may be provided through the mixing chamber. Further, threaded stoppers for the entrance ports may be provided.

DESCRIPTION OF THE DRAWINGS

A more complete appreciation of the invention and many of the attendant advantages thereof will be readily appreciated as the same becomes better understood by reference to the following detailed description when considered in connection with the accompanying drawings wherein:

FIG. 1 is a front elevational view of an administration set including the mixing chamber of the present invention;

FIG. 2 is a sectional view of the mixing chamber taken along line 2—2 of FIG. 1;

FIG. 3 is a sectional view of the mixing chamber taken along line 3—3 of FIG. 1;

FIG. 4 is a front sectional view of the mixing chamber of the present invention; and FIG. 5 is a front view partially in section of a portion of a mixing chamber illustrating the bypass and removeable stopper features.

DESCRIPTION OF THE PREFERRED EMBODIMENT

Referring now to the drawings wherein like reference characters designate corresponding or identical parts throughout the several views, and more particularly to FIG. 1., an administration set, generally denoted as 10, is shown. Four I.V. bottles 12, 14, 16 and 18 containing four different medical liquids, denoted liquids A, B, C and D, respectively, are suspended from a hanger 20 which itself is supported from a post 22 by a hook 24. Delivery tubes 26, 28, 30 and 32, which may be of polyethylene or other flexible plastic material are connected through fittings 34, 36, 38 and 40 to bottles 12, 14, 16 and 18, respectively. The opposite ends of delivery tubes 26, 28, 30 and 32 are connected to entry ports 42, 44, 46 and 48 (FIG. 4) respectively, of mixing chamber 50. Pinch valves 52, 54, 56 and 58 are disposed over delivery tubes 26, 28, 30 and 32 intermediate the respective bottle fittings and mixing chamber entry ports. A delivery tube 60 has one end connected to the exit port 62 of mixing chamber 50. A suitable needle 60 is attached to the other end of delivery tube 64 for insertion into the vein of the patient. A by-pass port 66 is provided in delivery tube 60 so that an additional medical liquid, such for example, as blood, may be added to the liquids being administered without the necessity of directing the same through mixing chamber 50. Thus, a liquid may be directed through a tube 68 having one end connected to port 66 and the other end directed to the liquid supply (not shown). A filter 69 is preferably interposed within the delivery tube 60.

Referring now to FIGS. 2 through 4, the mixing chamber 50 comprising the present invention is shown in detail. Mixing chamber 50 is preferably formed of a clear plastic material, such as polymerized methyl methacrylate. In the illustrated embodiment, the mixing chamber includes a front wall 70 and an opposed, substantially parallel rear wall 72. Front and rear walls 70, 72 are relatively thin and are relatively closely spaced to each other with respect to their transverse dimensions. Thus, by way of example only, front and rear walls 70, 72 each may have a thickness of about 1/16 inches, a height of about two inches and a width of about ½ inches. The distance between the inner surfaces of front and rear walls 70 and 72 may be about ¼ inches. Thus, it is clear that the interior of the mixing chamber defined by front and rear walls 70, 72 and the top and side walls, discussed below, is relatively shallow as best seen in FIGS. 2 and 3.

A top wall 74 extends between and is connected to the top peripheral edges of front and rear walls 70, 72 as by glue or the like. The four entry ports 42, 44, 46 and 48 are formed in top wall 74, each entry port having a bore formed therethrough providing fluid access to the interior of the chamber defined between front and rear walls 70, 72.

A side wall, generally denoted as 76, extends between and is connected to the side peripheral edges of front and rear walls 70, 72, as by glue or the like. Side wall 76 includes a pair of side portions 78 and a bottom portion 80. Exit port 62 is provided in bottom portion 80 of side wall 76 and has a bore formed therethrough which fluidly communicates with the chamber defined between front and rear walls 70, 72. Obviously, the thickness of the top and side walls 74 and 76 determine the spacing between the front and rear walls 70 and 72 and these dimensions are chosen such that the chamber defined by them is relatively shallow as described above.

As mentioned above, it is an object of the present invention to enable the early observation of any precipitation which may occur during the mixing of the medical liquids within the mixing chamber 50. To this end, a portion of front wall 70 is formed with a viewing portion or window 82 having a circular peripheral configuration and a convex cross section. When formed of a transparent material such as methyl methacrylate with the appropriate focal length in a manner well known in the art, such a window serves to magnify the area within mixing chamber 50, so that even the slightest amount of precipitation as evidenced by the initiation of a cloudiness or murkiness of the mixed liquids can be easily detected.

The particular configuration of the interior of mixing chamber 50, i.e., the shallowness of the space defined between the front, rear, top and side walls, promotes the mixing of the medical liquids so that any precipitation which may result from such mixing will be hastened. In order to further facilitate the complete mixing of the liquids, the side portions 78 of side wall 76 are formed with shoulders 84 which extend inwardly into the mixing chamber. Each of the shoulders 84 are defined by a generally convex, arcuate inner surface 86. Thus, each side portion 78 gradually increases in lateral dimension until a maximum is obtained at a point approximately half way between the top wall and the bottom of the mixing chamber. At that point, the lateral dimension of the side portion 78 begins to decrease. The provision of shoulders 84 promotes the turbulent mixing of the medical fluids entering mixing chamber 50 so that early precipitation is encouraged.

In operation, liquid A alone may be administered to the patient by opening valve 52 and closing valves 54, 56 and 58. Valve 54 may then be opened so that liquid B flows through delivery tube 28 into mixing chamber 50 where it completely mixes with liquid A by virtue of the above described structure of the mixing chamber. The physician will then observe the mixing through window 82 and any precipitation which may occur will be readily apparent as a cloudiness which appears in the mixture. If the physician determines that no precipitation has occurred, valve 56 may be opened to allow liquid C to enter mixing chamber 50 through delivery tube 30. Again, the mixture is observed through window 82. If precipitation occurs, valve 56 may be closed. A similar procedure is used to administer liquid D. In all cases, mixing chamber 50 allows an earlier detection of any incompatibility of the medical liquids in so far as precipitation is concerned by providing means for effecting a complete mixing of the medical liquids and ready observation of the mixing process. If and when it is determined that any of the liquids A–D cause the mixture to precipitate, the supply of that liquid may be cut off by closing the valve associated therewith.

Although the present invention has been described in conjunction with the administration of four different medical liquids, it is readily apparent that the present invention may be adapted to be used with a greater or lesser number of medical liquids. Further, although the mixing chamber 50 has been described as being constructed of clear plastic, other materials may be used so long as the window area 82, when used, is formed of a transparent material. The mixing chamber may be constructed from separate wall members as described or may be constructed in a unitary manner, i.e., with the front, rear, top and side (or any combination thereof) being intergrally formed.

Referring now to FIG. 5, a portion of a mixing chamber 100 incorporating additional features is illustrated. Mixing chamber 100 includes a sidewall 102 having a reduced diameter bore 104 formed therethrough which communicates with the bore of an entry port 106 at its upper end and an exit port 108 at its lower end. Any fluid directed into entry port 106 will bypass the interior of mixing chamber 100. As is readily apparent, this structure eliminates the need for a bypass port 66 in delivery tube 60 (FIG. 1).

Still referring to FIG. 5, the entry ports of the mixing chambers may be provided with removable stoppers. More particularly, when it is desired to use a needle connection to the mixing chamber as is well known in the art, the entry ports may be provided with external screw threads for connection with removable stoppers having corresponding internal threading. Thus, an entry port 110 may be provided with external threads 112. A stopper 114 including an internally threaded collar 116 and a rubber cap 118 may then be threadedly connected to port 110 until cap 118 seals the same. The medical liquid is introduced by inserting a needle through cap 118 as is well known in the art. Thus, the stoppers may be readily replaced after use of the mixing chamber.

The bypass and removable stoppers features illustrated in FIG. 5 may be used in conjunction with the mixing chamber of the present invention or may be used with conventional multi-ported chambers.

Obviously, numerous modifications and variations of the present invention are possible in the light of the above teachings. It is therefor to be understood that within the scope of the appended claim the invention may be practiced otherwise than as specifically described herein.

I claim:

1. A mixing chamber for use in an intravenous administration set wherein plural medical liquids are delivered to a patient comprising a pair of opposed, substantially parallely extending front and rear walls, said walls being closely spaced to each other relative to their transverse dimensions, said walls each having top and side peripheral edges;

a top wall extending between and interconnecting the top peripheral edges of said front and rear walls, said top wall having a plurality of entry ports formed therethrough, each port communicating with the space defined between said front and rear walls; and a side wall extending between and interconnecting the side peripheral edges of said front and rear walls, said side wall having an exit port formed therethrough, said exit port communicating with the space defined between said front and rear walls, whereby said front, rear, top and side walls define a relatively shallow interior chamber, said mixing chamber further including a bypass bore having upper and lower ends formed in said sidewall, the upper end of said bypass bore communicating with an entry port and the lower end of said bypass bore communicating with said exit port.

2. A mixing chamber as recited in claim 1 wherein said entry ports are provided with screw threads for connection to a threaded stopper member.

3. A mixing chamber comprising side and top walls defining an interior chamber, a plurality of entry ports formed in said top wall, an exit port formed in the lower region of said sidewall, and a bypass bore formed in said sidewall having upper and lower ends, the upper end communicating with one of said entry ports and the lower end communicating with said exit port.

4. A mixing chamber for use in an intravenous administration set wherein plural medical liquids are delivered to a patient comprising a pair of opposed, substantially parallely extending front and rear walls, said walls being closely spaced to each other relative to their transverse dimensions, said walls each having top and side peripheral edges;

a top wall extending between and interconnecting the top peripheral edges of said front and rear walls, said top wall having a plurality of entry ports formed therethrough, each port communicating with the space defined between said front and rear walls; and a side wall extending between and interconnecting the side peripheral edges of said front and rear walls, said side wall having an exit port formed therethrough, said exit port communicating with the space defined between said front and rear walls, whereby said front, rear, top and side walls define a relatively shallow interior chamber and further including means within said chamber for promoting mixing of said plural medical liquids.

5. A mixing chamber as recited in claim 4 wherein said mixing promoting means includes a pair of opposed side portions and a bottom portion defining said side wall, each of said side wall side portions having a shoulder extending inwardly into the chamber.

6. A mixing chamber as recited in claim 4 wherein said mixing promoting means includes a pair of opposed side portions and a bottom portion defining said side wall, each of said side wall portions gradually increasing in its inward dimension in the downward direction.

7. A mixing chamber as recited in claim 4 wherein said mixing promoting means includes a pair of opposed side portions and a bottom portion defining said side wall, each of said side wall side portions having a substantially convex inner surface.

* * * * *